United States Patent [19]

König

[11] Patent Number: 4,788,178
[45] Date of Patent: Nov. 29, 1988

[54] USE OF GONADOLIBERIN AND GONADOLIBERIN AGONISTS FOR THE TREATMENT OF CLIMACTERIC COMPLAINTS

[75] Inventor: Wolfgang König, Hofheim am Taunus, Fed. Rep. of Germany

[73] Assignee: Hoechst Aktiengesellschaft, Frankfurt, Fed. Rep. of Germany

[21] Appl. No.: 724,331

[22] Filed: Apr. 17, 1985

[30] Foreign Application Priority Data

Apr. 18, 1984 [DE] Fed. Rep. of Germany ....... 3414595

[51] Int. Cl.⁴ ............................................. A61K 37/02
[52] U.S. Cl. .................................................... 514/15
[58] Field of Search ......................... 514/15; 424/112

[56] References Cited

U.S. PATENT DOCUMENTS

| 4,118,483 | 10/1978 | König et al. | 514/15 |
| 4,263,282 | 4/1981 | von der Ohe et al. | 514/15 |
| 4,552,864 | 11/1985 | Antoni et al. | 514/15 |

OTHER PUBLICATIONS

Casper, *J. Clin. Endocrinol. Metab*, 53(5), 1981 (Abstract).
Cecil (ed), *A Textbook of Medicine*, 5th ed., W. B. Saunders Co., Philadelphia, 1941, p. 1359.
Casper et al., Journal of Clinical Endocrinology and Metabolism, vol. 53, No. 5, 1056–1058 (1981).
Atkinson et al., Klin Wochenschr (1984) 62: 129–132.
Dandona et al., J. Clin. Endocrinology and Metabolism, vol. 63, No. 2, 459–462 (1986).
Orwall et al., J. Clin. Endocrinology and Metabolism, vol. 63, No. 6, 1262 (1986).
Hall et al., Acta Endocrinologica, 108: 217–223, 1985.
McSheehy et al., Endocrinology, vol. 118, No. 2, 824–828 (1986).
Chambers et al., J. Endocr. 102, 281–286 (1984).
McSheehy et al., Endocrinology, vol. 119, No. 4, 1654–1659 (1986).
Anderson et al., Calcif. Tissue Int. 37: 646–650 (1985).
Hall et al., Pharmacology, 30: 339–347 (1985).
Orimo et al., Endocrinology, vol. 90: 760–763 (1972).
*Encyclopaedia Britannica*, Macropaedia, vol. 11, p. 907 (15th Edition).
*Encyclopaedia Brittanica*, Macropaedia, vol. 6, pp. 826–828 (15th Edition).
Schally et al., *Vitamins and Hormones*, vol. 38, pp. 270–294 (1980).
Law & Heath, *J. Clin. Endocr. Matab.*, 58:606–608 (1984).
Sakhaee et al., *J. Clin. Endocr. Matab.*, 61:368–373 (1985).
Johnston et al., *J. Clin. Endocr. Matab.* 61:905–911 (1985).
Lindgren & Lindholm, *Calcif. Tiss. Intl.*, 27:161–164 (1979).

*Primary Examiner*—Ronald W. Griffin
*Assistant Examiner*—F. T. Moezie
*Attorney, Agent, or Firm*—Finnegan, Henderson, Farabow, Garrett, & Dunner

[57] ABSTRACT

The invention relates to the use of gonadoliberin and gonadoliberin agonists for the treatment of climacteric complaints and pathological conditions in which the level of parathyroid hormone is elevated, and to preparations containing this or these compounds(s).

9 Claims, 1 Drawing Sheet

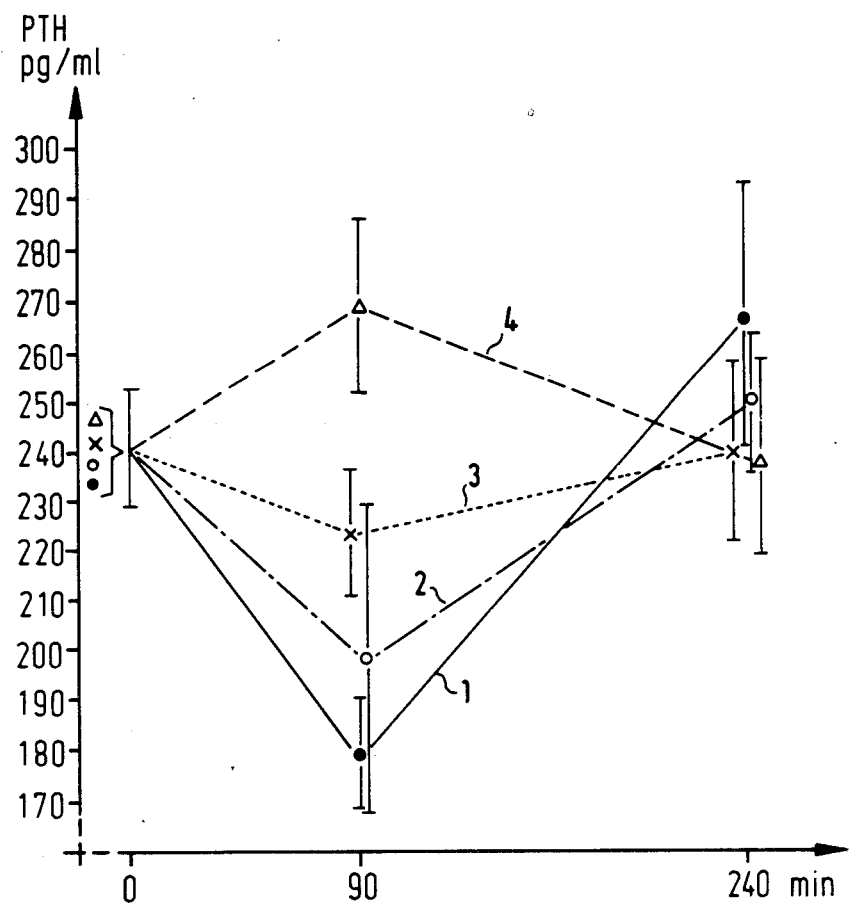

USE OF GONADOLIBERIN AND GONADOLIBERIN AGONISTS FOR THE TREATMENT OF CLIMACTERIC COMPLAINTS

It has been found that gonadoliberin and its analogs having agonistic actions exert an advantageous effect, surprisingly in low doses, on both premenopausal and postmenopausal climacteric complaints.

Thus the invention relates to the use of gonadoliberin or its agonistic analogs which are at least as active, and to pharmaceutical preparations which comprise a pharmacologically effective content of this or these compound(s) in a pharmaceutically acceptable vehicle, for the treatment of climacteric complaints and pathological conditions in which the level of parathyroid hormone is too high.

Increased levels of parathyroid hormone are found in bone marrow in cases of osteoporosis (Klin. Wochenschr. 62, 129–132, 1984); parathyroid hormone has an osteolytic effect. In young female rats with a high level of parathyroid hormone, small doses of the gonadoliberin agonist buserelin reduced parathyroid hormone in the plasma, although a parathyroid hormone level which has been reduced by infusion of calcium is raised by similar doses of buserelin (see German Patent Application No. P 33 32 329.1). It is possible that this regulating action of buserelin on parathyroid hormone plays a part in the treatment of ostalgia and osteoporosis.

The complaints which can be treated with gonadoliberin or its agonistic analogs are disturbances of the cycle (irregular menstruation) in the premenopause, postclimacteric complaints such as, for example, hot flushes, rigors, sweats, dizziness, palpitations, insomnia, anxiety, depression, headaches and ostalgia, and osteoporosis and renal insufficiency. The level of parathyroid hormone is elevated in both osteoporosis (Klin. Wochenschr. 62 [1984] 129–132) and renal insufficiency (Akt. Endokr.Stoffw. 5 [1984] 180–186).

Gonadoliberin is a decapeptide of the formula I, is formed in the hypothalamus, and brings about the release of follitropin and lutropin in the pituitary (Biochem. Biophys. Res. Commun. 43, 1971, page 1334).

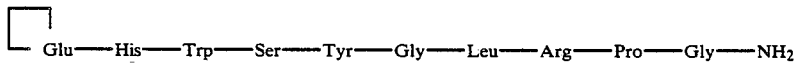

(I)

The diagnostic dose of gonadoliberin to release the gonadotropins (follitropin and lutropin) on parenteral administration is 25–100 μg/adult human (Rote Liste 1983, 34002 and 24004). The intranasal dosage used for cryptorchidism in children between two and six years of age is 3×400 μg each day (Rote Liste 1983, 49038).

In contrast, in the method according to the invention for the treatment of climacteric complaints, parenteral administrations of only 0.5–5 μg of gonadoliberin suffice for a woman of normal weight (=6 to 60 ng/kg/dose). On intranasal administration, because of the poor absorption, about 10–200 μg of gonadoliberin are administered to a woman of normal weight. In general, 2–3 doses are given each day at the start of the treatment. After the complaints have subsided, it is possible to limit administration to once a day.

The agonistic action of gonadoliberin is particularly potentiated by substitution of Gly—$NH_2^{10}$ by the ethylamine radical, and by replacement of $Gly^6$ by lipophilic D-amino acids. In this way, compounds which, depending on the assay, have actions which are about 100–200 times as potent as that of gonadoliberin are obtained (Vitamins and Hormones 38, 1980, pages 257–323). It is important for the replacement in position 6 that the D-amino acid contains an α—CH and a β—$CH_2$ group (Peptides Chemistry, Structure, Biology, pages 883–888, Ann Arbor Science Publishers Inc, Ann Arbor, Mich. 1975). Of the "natural" D-amino acids, D-Trp, D-Leu and the tert.-butyl ether of D-Ser have proved most useful. However, even higher activities can be obtained by use of synthetic aromatic D-amino acids such as, for example, with [D-3-(2,4,6-trimethylphenyl)-$Ala^6$]- and [D-3-(2-naphthyl)$Ala^6$]-gonadoliberin (J. Med. Chem. 25, 1982, pages 795–801).

All gonadoliberin analogs whose activity is as much as or higher than that of gonadoliberin are suitable for the indication. For example, the following analogs of the formula II are suitable:

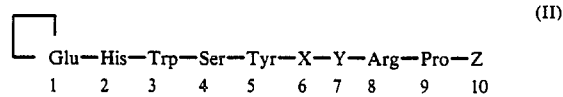

(II)

in which (for abbreviations, see Houben-Weyl, Methoden der organischen Chemie (Methods of Organic Chemistry), 4th edition, Vol. XV/1 and XV/2, published by Thieme, Stuttgart):

(a)
Z denotes Gly—$NH_2$,
Y denotes Leu, and
X denotes D-Nle, D-Nva, D-Abu, D-Phe, D-Ser, D-Met, D-Pgl, D-Lys, D-Leu, D-Arg, D-Ser(Bu$^t$), D-Thr(Bu$^t$), D-Cys(Bu$^t$), D-Lys, D-Asp, D-Asp(OBu$^t$), D-Glu(OBu$^t$), D-Orn(Boc), D-Lys(Boc), D-Trp, D-Tyr, ε-lauryl-D-Lys or ε-dextran-D-Lys, D-His(Bzl) or (b)
Z denotes Gly—$NH_2$, NH—($C_1$–$C_3$)-alkyl or NH-cyclopropyl, which can be substituted by OH or F,
Y denotes Leu, Ser(Bu$^t$), Cys(Bu$^t$), Glu(OBu$^t$), Orn(Boc) or Lys(Boc), and
X denotes D-Ser(Bu$^t$), D-Cys(Bu$^t$), D-Asp(OBu$^t$), D-Glu(OBu$^t$), D-Orn(Boc) or D-Lys(Boc), D-His(Bzl)

$Ser^4$ optionally being replaced by Ala or Thr, Tyr optionally being replaced by Phe, and Arg optionally being replaced by Orn, Lys or homoarginine, or (c)
Z denotes —$NHCH_3$, —NH—$CH_2$—$CH_3$, —NH—$CH_2CH_2CH_3$, —$NHCH_2CH_2$—OH, 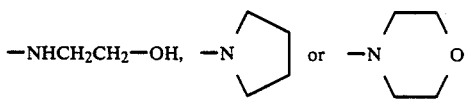

Y denotes Leu, and
X denotes Gly or (d)
Z denotes —$NHC_2H_5$,

Y denotes Leu, and

X denotes D-Trp, D-Leu, D-Ala, D-Ser(Bu$^t$), D-Tyr, D-Lys or D-His(Bzl) or (e)

Z denotes Gly—NH$_2$ or NH—C$_2$H$_5$,

Y denotes N-α-methyl-Leu, and

X denotes Gly or (f)

Z denotes NH-cyclopropyl,

Y denotes Leu, and

X denotes D-Leu or (g)

Z denotes Gly—NH$_2$, NH—(C$_1$–C$_3$)-alkyl or NH-cyclopropyl,

Y denotes Ser(Bu$^t$), Cys(Bu$^t$), Asp(OBu$^t$), Glu(OBu$^t$), Orn(Boc) or Lys(Boc), and X denotes Gly.

Compounds of the formula II and processes for their preparation are disclosed in, for example:

COY D. H., LABRIE F., FAVARY M., COY E. J. and SCHALLY A. V. (1975) LH - releasing activity of patent LH - RH analogs in vitro BBRC 67, 576–582.

Wylie Vale et al. (1976) in "Hypothalamus and endocrine functions" (F. LABRIE, J. MEITES and G. PELLETIER, eds; PLENUM Press) pages 397–429.

FUJINO, BBRC vol. 49, No. 3, 1972, page 863. German Offenlegungsschrift No. 2,509,783, U.S. Pat. Nos. 3,901,872, 3,896,104, Japanese Pat. No. 4 9100-081, U.S. Pat. No. 3,971,737, Belgian Pat. No. 842,857, Belgian Pat. Nos. 832,310, 832,311, 4,003,884, 4,024,248, German Offenlegungsschrift Nos. 2,720,245, 2,446,005.

The following analogs have proved to be particularly suitable, for example:

[D-Ser(Bu$^t$)$^6$]-gonadoliberin-(1-9)-nonapeptide ethylamide (=buserelin) (Drugs of the Future 4, 1979, pages 173–177, 8, 1983 page 254),

[D-Trp$^6$]-gonadoliberin (Drugs of the Future 3, 1978, pages 645–646),

[D-Trp$^6$]-gonadoliberin-(1-9)-nonapeptide ethylamide (Drugs of the Future 7, 1982, pages 637–642),

[D Leu$^6$]-gonadoliberin-(1-9)-nonapeptide ethylamide (Drugs of the Future 7, 1982, pages 882–886),

[D-Ser(Bu$^t$)$^6$, AzaGly$^{10}$]-gonadoliberin (Drugs of the Future 5, 1980, pages 191–192; 1983, pages 364–365),

[D-Trp$^6$, N-MeLeu$^7$]-gonadoliberin-(1-9)-nonapeptide ethylamide (Drugs of the Future 8, 1983, pages 347–350),

[δ-tert.-butyl ester of D-α-aminoadipic acid$^6$]-gonadoliberin-(1-9)-nonapeptide ethylamide (German Offenlegungsschrift No. 3,020,941) and the analogs containing the unnatural D-amino acids which were listed above in the introduction.

BRIEF DESCRIPTION OF THE DRAWING

FIG. 1 sets forth the action of Buserelin on parathyroid hormone levels in blood serum.

The preparations according to the invention can be administered intranasally or parenterally. For a form for intranasal administration, the compound is mixed with the additives customary for this purpose, such as stabilizers or inert diluents, and converted by customary methods into suitable administration forms, such as aqueous, alcoholic or oily suspensions or aqueous, alcoholic or oily solutions. Examples of suitable oily vehicles or solvents are vegetable or animal oils, such as sunflower oil or fishliver oil.

For subcutaneous or intravenous administration, the active compound or its physiologically tolerated salts are converted into a solution, suspension or emulsion, where desired with the substances customary for this purpose, such as solubilizers, emulsifiers or other auxiliaries.

Examples of suitable solvents are: water, physiological sodium chloride solutions or alcohols, for example ethanol, propanediol or glycerol, as well as sugar solutions, such as glucose or mannitol solutions, as well as a mixture of the various solvents mentioned.

The LH-RH analogs which are specifically listed here are all highly active. Their activity in humans is about 10 times that of gonadoliberin, and their duration of action is longer. Thus, they must be administered in lower doses than and not as often as gonadoliberin. On parenteral administration, 50 to 500 ng of the above-mentioned gonadoliberin agonists usually suffice for a woman of normal weight ($\approx 0.6$ to 70 ng/kg/dose). On administration onto the mucosa (for example intranasal administration), 1–20 μg of analog are necessary for an adult of normal weight ($\approx 10$ to 300 ng/kg/dose). However, it may also be necessary to lower the dose of particularly highly active LH-RH-analogs or to increase the dose of those which are less active.

EXAMPLE 1

(Preparation for Intranasal Administration)

4.0 g of Glu-His-Trp-Ser-Tyr-D-Ser(Bu$^t$)-Leu-Arg-Pro-NH-C$_2$H$_5$ diacetate are dissolved in 100 ml of distilled water. At the same time, 31.2 g of NaH$_2$PO$_4$·2H$_2$O, 66.29 g of Na$_2$HPO$_4$, 25 g of NaCl and 100 g of benzyl alcohol are dissolved in 8 l of distilled water, and 500 g of polyvinyl alcohol with a K value of about 90 are added. The two solutions are combined and filtered.

EXAMPLE 2

(Preparation for Intranasal Administration)

100 g of anhydrous lanolin and 440 g of vaseline are melted together. A suspension of 800 mg of microfine Glu-His-Trp-Ser-Phe-D-Glu(OBu$^t$)-Leu-Arg-Pro-NH-C$_2$H$_5$ diacetate in 359.2 g of liquid paraffin is added to the cooled melt. Finally, 10 g of benzyl alcohol are added, and the ointment is homogenized.

EXAMPLE 3

(Preparation for Injections)

2 mg of Glu-His-Trp-Ser-Tyr-D-Lys(Boc)-Leu-Arg-Pro-NH-C$_2$H$_5$ diacetate are dissolved in 500 ml of double-distilled water, and 100 ml of phosphate buffer, pH 4.5, are added. Then 1 g of mannitol and the calculated amount of NaCl for isotonicity are added, and the volume is made up to 1 liter with water. After sterilization by filtration, the product is filled into 1 or 2 ml ampoules and is freeze-dried.

EXAMPLE 4

(Preparation for Injections)

The process is carried out as in Example 3, but 2.5 g of methyl 4-hydroxybenzoate are added before the volume is made up with water. After sterilization by filtration, the product is filled into 1 or 2 ml ampoules.

EXAMPLE 5

Buserelin is advantageously administered intranasally at a dose of 1 to 10 μg to a woman of normal weight.

One dose a day is given until the complaints have disappeared. Subsequently, it is possible to continue the treatment with one administration every second day.

This treatment can also be employed for complaints in the male climacteric.

EXAMPLE 6

Action of buserelin to lower parathyroid hormone (see FIG. 1)

4 groups each containing 5 female Wistar rats were treated with placebo or three different doses (1 ng/kg, 5 ng/kg and 50 ng/kg) of buserelin. An initial blood sample was taken from all animals (initial value). Thereafter, the animals were given an injection of buserelin in physiological sodium chloride solution with the addition of 0.25% Haemaccel$^R$, and the placebo group was given the same amount of physiological sodium chloride solution with the addition of 0.25% Haemaccel$^R$. Blood samples were taken after 90 minutes and 240 minutes. The blood serum was investigated for parathyroid hormone. After 90 minutes, the level of parathyroid hormone decreased in the buserelin group, the best effect being observed at the low doses. The initial value had been regained after 240 minutes. Explanation of the FIG. 1: The time course of the PTH level after i.v. administration of 1 ng/kg buserelin (curve 1), 5 ng/kg (curve 2) and 50 ng/kg (curve 3) is shown. Curve 4 shows the course on administration of placebo. All measurements are indicated with standard deviation (n=5).

EXAMPLE 7

A woman (47 years old) with irregular menstruation and severe cramp-like pains during the period, together with persistent pressure on the bladder and the typical hot flushes, was treated twice a day (in the morning and evening) with 100 μg of gonadoliberin (intranasal). The complaints had already disappeared after the 1st day of treatment. The patient was treated for about 9 months. Menstruation occurred very punctually during this period.

The treatment was discontinued twice for two weeks in each instance. However, the abovementioned complaints recurred during this, so that treatment was continued in accordance with the regimen described above. No adverse reactions to gonadoliberin were observed.

EXAMPLE 8

A woman (35 years old) started to have severe attacks of migraine and ostalgia following surgical removal of the uterus. It was possible to improve both symptoms by treatment with 50 μg of gonadoliberin (intranasal) twice a day. The ostalgia was reduced to a minimum, and the attacks of migraine were briefer, rarer and considerably less intense than without gonadoliberin treatment.

I claim:

1. A method for the treatment of climacteric complaints and pathological conditions in which the level of parathyroid hormone is too high, comprising administering to a patient in need of treatment of said complaints and conditions, a pharmacologically effective amount of gonadoliberin or a pharmacologically effective amount of a gonadoliberin agonist of formula II:

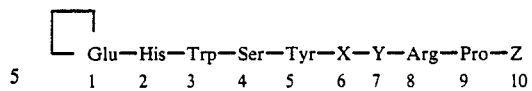

(II)

in which (a)
  Z denotes Gly—NH$_2$,
  Y denotes Leu, and
  X denotes D-Nle, D-Nva, D-Abu, D-Phe, D-Ser, D-Met, D-Pgl, D-Lys, D-Leu, D-Arg, D-Ser(Bu$^t$), D-Thr(Bu$^t$), D-Cys(Bu$^t$), D-Asp, D-Asp(OBu$^t$), D-Glu(OBu$^t$), D-Orn(Boc), D-Lys(Boc), D-Trp, D-Tyr, ε-lauryl-D-Lys or ε-dextran-D-Lys, D-His(Bzl) or (b)
  Z denotes Gly—NH$_2$, NH—(C$_1$–C$_3$)-alkyl or NH-cyclopropyl, which can be substituted by OH or F,
  Y denotes Leu, Ser(Bu$^t$), Cys(Bu$^t$), Glu(OBu$^t$), Orn(Boc) or Lys (Boc), and
  X denotes D-Ser(Bu$^t$), D-Cys(Bu$^t$), O-Asp(OBu$^t$), D-Glu(OBu$^t$), D-Orn(Boc) or D-Lys(Boc), D-His(Bzl)

or said, agonist wherein Ser$^4$ is replaced by Ala or Thr, or wherein Tyr is replaced by Phe, or wherein Arg is replaced by Orn, Lys or homoarginine, or (c)
  Z denotes —NHCH$_3$, —NH—CH$_2$—CH$_3$, —NH—CH$_2$CH$_2$CH$_3$,

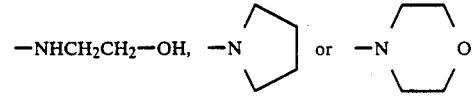

Y denotes Leu, and
  X denotes Gly or (d)
  Z denotes —NHC$_2$H$_5$,
  Y denotes Leu, and
  X denotes D-Trp, D-Leu, D-Ala, D-Ser(Bu$^t$), D-Tyr, D-Lys or D-His(Bzl) or (e)
  Z denotes Gly—NH$_2$ or NH—C$_2$H$_5$,
  Y denotes N-α-methyl-Leu, and
  X denotes Gly or (f)
  Z denotes NH-cycloporpyl,
  Y denotes Leu, and
  X denotes D-Leu or (g)
  Z denotes Gly—NH$_2$, NH—(C$_1$–C$_3$)-alkyl or NH-cyclopropyl,
  Y denotes Ser(Bu$^t$), Cys(Bu$^t$), Asp(OBu$^t$), Glu(OBu$^t$), Orn(Boc) or Lys(Boc), and
  X denotes Gly.

2. A method for the treatment of osteoporosis in which the level of parathyroid hormone is too high, comprising administering to a patient in need of treatment for said osteoporosis, a pharmacologically effective amount of gonadoliberin or a pharamacologically effective amount of a gondoliberin agonist of formula II:

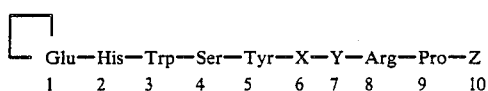 (II)

Glu—His—Trp—Ser—Tyr—X—Y—Arg—Pro—Z
 1    2    3   4   5  6 7  8   9  10 in which
(a)
 Z denotes Gly—NH$_2$,
 Y denotes Leu, and
 X denotes D-Nle, D-Nva, D-Abu, D-Phe, D-Ser, D-Met, D-Pgl, D-Leu, D-Arg, D-Ser(Bu$^t$), D-Thr(Bu$^t$), D-Cys(Bu$^t$), D-Lys, D-Asp, D-Asp(OBu$^t$), D-Glu(OBu$_t$), D-Orn(Boc), D-Lys(Boc), D-Trp, D-Tyr, ε-lauryl-D-Lys or ε-dextran-D-Lys, D-His(Bzl) or
(b)
 Z denotes Gly—NH$_2$, NH—(C$_1$–C$_3$)-alkyl or NH-cyclopropyl, which can be substituted by OH or F,
 Y denotes Leu, Ser(Bu$^t$), Cys(Bu$^t$), Glu(OBu$^t$), Orn(Boc) or Lys(Boc), and
 X denotes D-Ser(Bu$^t$), D-Cys(Bu$^t$), D-Asp(OBu$^t$), D-Glu(OBu$^t$), D-Orn(Boc) or D-Lys(Boc), D-His(Bzl)

or said agonist wherein Ser$^4$ is replaced by Ala or Thr, or wherein Tyr is replaced by Phe, or wherein Arg is replaced by Orn, Lys or homoarginine, or
(c)
 Z denotes —NHCH$_3$, —NH—CH$_2$—CH$_3$, —NH—CH$_2$CH$_2$CH$_3$,

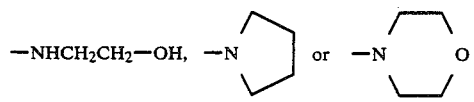

Y denotes Leu, and
 X denotes Gly or
(d)
 Z denotes —NHC$_2$H$_5$,
 Y denotes Leu, and
 X denotes D-Trp, D-Ala, D-Ser(Bu$^t$), D-Tyr, D-Lys or D-His(Bzl)
(e)
 Z denotes Gly—NH$_2$ or NH—C$_2$H$_5$.
 Y denotes N-α-methyl-Leu, and
 X deontes Gly
(f)
 Z denotes NH-cyclopropyl,
 Y denotes Leu, and
 X denotes D-Leu or
(g)
 Z denotes Gly—NH$_2$, NH—(C$_1$–C$_3$)-alkyl or NH-cyclopropyl,
 Y denotes Ser(Bu$^t$), Cys(Bu$^t$), Asp(OBu$^t$), Glu(OBu$^t$), Orn(Boc) or Lys (Boc), and
 X denotes Gly.

3. A method for the treatment of renal insufficiency in which the level of parathyroid hormone is too high, comprising adminstering to a patient in need of treatment for said renal insufficiency a pharamcologically effective amount of gonadoliberin or a pharamcologically effective amount of a gonadoliberin agonist of formula II:

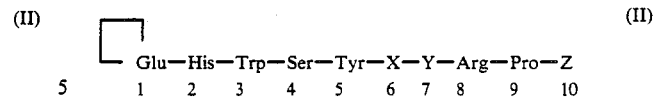 (II)

Glu—His—Trp—Ser—Tyr—X—Y—Arg—Pro—Z
 1    2    3    4   5  6 7   8   9  10 in which
(a)
 Z denotes Gly—NH$_2$,
 Y denotes Leu, and
 X denotes D-Nle, D-Abu, D-Phe, D-Ser, D-Met, D-Pgl, D-Lys, D-Leu, D-Arg, D-Ser(Bu$^t$), D-Thr(Bu$^t$), D-Cys(Bu$^t$), D-Asp, D-Asp(OBu$^t$), D-Glu(OBu$^t$), D-Orn(Boc), D-Lys(Boc), D-Trp, D-Tyr, ε-lauryl-D-Lys or ε-dextran-D-Lys, D-His(Bzl) or
(b)
 Z denotes Gly—NH$_2$, NH—(C$_1$–C$_3$)-alkyl or NH-cyclopropyl, which can be substituted by OH or F,
 Y denotes Leu, Ser(Bu$^t$), Cys(Bu$^t$), Glu(OBu$^t$), Orn(Boc) or Lys(Boc), and
 X denotes D-Ser(Bu$^t$), D-Cys(Bu$^t$), D-Asp(OBu$^t$), D-Glu(OBu$^t$), D-Orn(Boc) or D-Lys(Boc), D-His(Bzl)

or said agonist wherein Ser$^4$ is replaced by Ala or Thr, or wherein Tyr is replaced by Phe, or wherein Arg is replaced by Orn, Lys or homoarginine, or
(c)
 Z denotes —NHCH$_3$, —NH—CH$_2$—CH$_3$, —NH—CH$_2$CH$_2$CH$_3$,

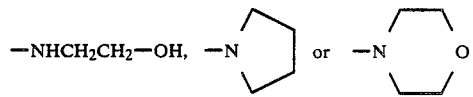

Y denotes Leu, and
 X denotes Gly or
(d)
 Z denotes —NHC$_2$H$_5$,
 Y denotes Leu, and
 X denotes D-Trp, D-Leu, D-Ala, D-Ser(Bu$^t$), D-Tyr, D-Lys or D-His(Bzl) or
(e)
 Z denotes Gly—NH$_2$ or NH—C$_2$H$_5$,
 Y denotes N-α-methyl-Leu, and
 X denotes Gly or
(f)
 Z denotes NH-cyclopropyl,
 Y denotes Leu, and
 X denotes D-Leu or
(g)
 Z denotes Gly—NH$_2$, NH—(C$_1$–C$_3$)-alkyl or NH-cyclopropyl,
 Y denotes Ser(Bu$^t$), Cys(Bu$^t$), Asp(OBu$^t$), Glu(OBu$^t$), Orn(Boc) or Lys(Boc), and
 X denotes Gly.

4. The method of claim 1 wherein said administering comprises parenterally administering 6 to 60 ng/kg of gonadoliberin pre single dose or an equally effective amount of said gonadoliberin agonist of formula II to said patient.

5. The method of claim I wherein said administering comprises administering 0.12 to 2.4 micrograms/kilogram of gonadoliberin pre single dose or an equally effective amount of said gonadoliberin agonist of formula II onto the mucosa of said patient.

6. The method of claim 2 wherein said administering comprises parenterally administering 6 to 60 ng/kg of gonadoliberin per single dose or an equally effective amount of said gondoliberin agonist of formula II to said patient.

7. The method of claim 2 wherein said administering comprises administering 0.12 to 2.4 micrograms/kilogram of gonadoliberin per single dose or an equally effective amount of said gonadoliberin agonist of formula II onto the mucosa of said patient.

8. The method of claim 3 wherein said administering comprises parenterally administering 6 to 60 ng/kg of gonadoliberin per single dose or an equally effective amount of said gonadoliberin agonist of formula II to said patient.

9. The method of claim 3 wherein said administering comprises administering 0.12 to 2.4 micrograms/kilogram of gonadoliberin per single dose or an equally effective amount of said gonadoliberin agonist of formula II onto the mucosa of said patient.

* * * * *